(12) United States Patent
Gu et al.

(10) Patent No.: US 9,205,071 B2
(45) Date of Patent: Dec. 8, 2015

(54) ARSENIC COMPOUNDS, THEIR PREPARATION METHODS AND USES THEREOF

(75) Inventors: Shuhua Gu, Changzhou (CN); Xuecheng Wang, Changzhou (CN)

(73) Assignee: Changzhou Hi-Tech District Multiple Dimension Industry Technology Institute Co., Ltd., Changzhou (CN)

( * ) Notice: Subject to any disclaimer, the term of this patent is extended or adjusted under 35 U.S.C. 154(b) by 1076 days.

(21) Appl. No.: 13/318,047

(22) PCT Filed: Apr. 16, 2010

(86) PCT No.: PCT/CN2010/000518
§ 371 (c)(1),
(2), (4) Date: Oct. 28, 2011

(87) PCT Pub. No.: WO2010/124522
PCT Pub. Date: Nov. 4, 2010

(65) Prior Publication Data
US 2012/0039995 A1    Feb. 16, 2012

(30) Foreign Application Priority Data

May 1, 2009    (CN) .......................... 2009 1 0027420

(51) Int. Cl.
*A61K 31/285*    (2006.01)
*C07C 229/22*    (2006.01)
(52) U.S. Cl.
CPC ............. *A61K 31/285* (2013.01); *C07C 229/22* (2013.01)

(58) Field of Classification Search
CPC ........................... A61K 31/285; C07C 229/22
See application file for complete search history.

(56) References Cited

U.S. PATENT DOCUMENTS 4,935,450 A * 6/1990 Cone, Jr. .................. 514/728

FOREIGN PATENT DOCUMENTS

| CN | 1625407 A | | 6/2005 |
|---|---|---|---|
| CN | 1625407 A | * | 6/2005 |
| WO | WO-2006107794 A2 | | 10/2006 |

* cited by examiner

*Primary Examiner* — Seal Basquill
*Assistant Examiner* — Andrew S Rosenthal
(74) *Attorney, Agent, or Firm* — Drinker Biddle & Reath LLP

(57) ABSTRACT

Arsenic compounds of general formula (I), their preparation methods, the pharmaceutical compositions containing the compounds, and their uses in the manufacture of medicaments for treating cancer, particularly leukemia, are disclosed.

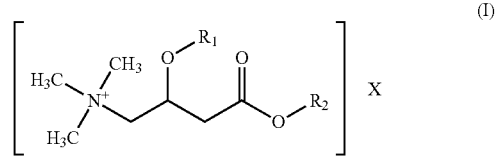

(I)

21 Claims, No Drawings

ARSENIC COMPOUNDS, THEIR PREPARATION METHODS AND USES THEREOF

CROSS-REFERENCE TO RELATED APPLICATIONS

This application is a national stage application (under 35 U.S.C. §371) of PCT/CN2010/000518, filed on Apr. 16, 2010, which claims benefit of Chinese application CN 200910027420.8, filed on May 1, 2009, both of which are incorporated herein by reference in their entirety for all their useful purposes.

FIELD OF THE INVENTION

The present invention relates to an arsenic compound, preparation method and use for the therapy of cancer thereof.

BACKGROUND OF THE INVENTION

Arsenic compounds are contained in many traditional Chinese medicines such as arsenolite, arsenic, realgar, orpiment. Arsenic Compounds have been used for treating skin diseases, such as syphilis in Traditional Chinese Medicine (TCM) from long time ago. Arsenic Compounds were used for cancer therapy since 19 century; e.g. Lissauer et. al used 1% potassium arsenite solution (Fowler solution) for treating leukemia. In 1971, Han, Taiyun, from The First Affiliated Hospital of Haerbing Medical College, had developed a medicine for treating leukemia by improving a kind of TCM containing arsenic. Zhang Tingdong, Zhang Peng., et. al used "Ailing yihao" to treat chronic myeloid leukemia in 1973, which has improved the blood parameters and the clinical symptoms of the patients. However, $As_2O_3$ injection is highly toxic, carcinogenic, teratogenic, and mutagenic. It may cause nausea, vomit and leukopenia etc side effects (Zhao Ningli et. al., Clinical Oncology, 2005, 10(1): 87-88); Myelosuppression is another side effect after a long-term administration (Li Fang., et. al., Foreign Medicine: Traditional Chinese Medicine Volume, 2001, 23(3): 134-138). In addition, $As_2O_3$ is slightly soluble in water, has poor water solubility and poor bioavailability. At present, no satisfied drug is found for clinically treating leukemia. Therefore, there is a need to further develop a new compound with effectively reduced toxicity and side effects of $As_2O_3$, increased solubility and bioavailability, and enhanced efficacy of anti-cancer.

SUMMARY OF THE INVENTION

One object of the present invention is to provide an arsenic compound which can effectively treat cancer, and to provide a preparation method thereof and a composition containing the same.

An arsenic compound of the present invention has a structure of following formula (I):

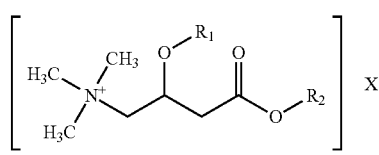

Wherein $R_1$ is independently selected from H, linear or branched $C_2$-$C_{20}$ alkylacyl groups, or $C_7$-$C_{12}$ phenylalkylacyl groups; $R_2$ is independently selected from H, linear or branched $C_2$-$C_8$ alkyl groups, or $C_7$-$C_{12}$ phenylalkyl groups; X is selected from $H_2AsO_4^-$, $HLiAsO_4^-$, $HKAsO_4^-$, $HNaAsO_4^-$, $Li_2AsO_4^-$, $K_2AsO_4^-$, $Na_2AsO_4^-$, $CaAsO_4^-$, $MgAsO_4^-$, $AsO_2^-$, $(NH_4)_2AsO_4^-$, and $(NH_4)HAsO_4^-$.

A salt of the following structure of formula (II) formed by arsenic acid and a carnitine derivative is preferred in the present invention.

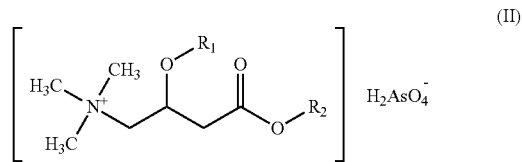

Wherein $R_1$ is independently selected from H, linear or branched $C_2$-$C_{20}$ alkylacyl groups, or $C_7$-$C_{12}$ phenylalkylacyl groups; $R_2$ is independently selected from H, linear or branched $C_2$-$C_8$ alkyl groups, or $C_7$-$C_{12}$ phenylalkyl groups. Preferably, $R_1$ is selected from acetyl, propionyl, butyryl, valeryl, isovaleryl, lauroyl, tetradecanoyl, palmitoyl, stearyl, benzoyl, phenylacetyl, phenyl propionyl, phenyl butyryl, phenyl valeryl or phenyl isovaleryl; $R_2$ is selected from ethyl, propyl, butyl, pentyl, isopentyl, benzyl, phenethyl, phenylpropyl, phenylbutyl, phenylpentyl or phenylisopentyl.

The compound shown by Formula (II) includes a levoisomer, a dextroisomer and a racemate thereof, wherein a levoisomer of the compound is particularly preferred.

A method for preparing an arsenic compound or a crystal thereof of the present invention includes the steps of:
a) dissolving a compound of formula (III) in an organic solvent to form a solution;

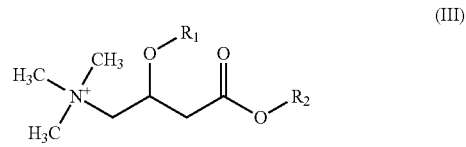

b) dropwise adding arsenic acid or optionally a compound X of claim 1 into the solution obtained in step a) under stirring;
c) separating out a salt of formula (II);
d) crystallizing the salt of step c) in an organic solvent to obtain a crystal of the arsenic compound.

Another object of the present invention is to provide a pharmaceutical composition for treating cancers. Wherein the said cancers include liver cancer, lung cancer, pancreatic cancer, breast cancer, cervical cancer, endometrial cancer, large intestinal cancer, stomach cancer, kidney cancer, nasopharyngeal cancer, ovarian cancer, prostate cancer, chronic or acute leukemia, brain cancer, esophagus cancer, oral cancer, cardia cancer, colon cancer, gallbladder cancer, laryngocarcinoma, gingival carcinoma, urethral carcinoma, skin cancer, rectal cancer, cancer of middle ear, bone cancer, testicular cancer, cancer of endocrine system, lymphocytic lymphoma, primary CNS lymphoma, chordoma, pituitary adenoma, or a combination one or more of the above mentioned cancers. Preferably, the said cancer is leukemia. The pharmaceutical composition of the present invention contains therapeutically effective amount of arsenic compound of the present invention and a pharmaceutical carrier.

The pharmaceutical composition of the present invention containing therapeutically effective amount of the compound of formula (II) is particularly preferred.

The arsenic compounds and compositions thereof in the present invention can be made into different pharmaceutical formulations, which include oral preparations, injections or topical preparations, wherein:

(1) The oral preparations include ordinary tablets, sustained release tablets, granules, hard or soft capsules, syrups, solutions, emulsions. Carriers of the oral preparations include fillers, disintegrating agents, adhesives, lubricants, coloring agents, flavoring agents or other conventional additives, which specifically include starch, lactose, microcrystalline cellulose, sodium carboxymethyl starch, crosslinked polyvinylpyrrolidone, polyvinylpyrrolidone, hydroxypropyl methylcellulose, magnesium stearate, silica and polysorbate 80, and sodium lauryl sulfate.

(2) The injections include sterile aqueous solutions for injection, sterile oil-in-water microemulsions for injection, and sterile powders for injection. Carriers of the injections include solvents for injection, and additives for injection, and the solvents for injection specially include water for injection, oils for injection, such as soybean oil, solubilizers for injection such as ethanol, propylene glycol, polyethylene glycol, glycerin, and isotonic substances such as sodium chloride, glucose.

(3) The topical preparations are patches, suppositories, creams, ointments, gels, solutions, suspensions or targeting preparations, wherein the said targeting preparations include liposomes, microspheres, nanoparticles, inclusions, and conjugates of monoclonal antibodies. Carriers of topical preparations include conventional pharmaceutical carriers used for topical administration.

A method for administering a pharmaceutical formulations includes intravenous administration, intramuscular administration, intraperitonea administrationl, subcutaneous administration oral administration, rectal suppository insertion method, intravaginal suppository insertion method, targeted drug delivery, inhalation, gavage, nasal feeding, sublingual administration, dripping method, micro-needle administration, continuous drug delivery system, and topical administration.

A method for topical administration includes transdermal preparations or implantable continuous drug release system. Wherein, the carrier for transdermal preparations includes framework materials such as hydrophobic polysiloxane, hydrophilic polyvinyl alcohol etc; controlled release membrane materials such as polysiloxane, ethylene-vinyl acetate copolymer etc; pressure-sensitive adhesives such as polyisobutylene, polysiloxane and polyacrylate, active ingredients being generally dispersed in the pressure-sensitive adhesives; polymer materials for the implantable continuous drug release system include polylactic acid glycolic acid copolymer, polyethylene glycol polylactic acid copolymers, polylactic acid/polycaprolactone, poly[(tetramethylene-co-$\epsilon$-caprolactone) carbonate], poly-butyrolactone valerolactone, polydioxanone (PDS), poly-3-hydroxybutyrate (PHB), poly-L-lactic acid (PLLA), polyglycolic acid (PGA), poly-$\epsilon$-caprolactone(PCL), polycaprolactone/poly(glycolide-co-lactide) (PCUPLGA), hydroxyethyl methacrylate (HEMA).

When administered to human, the daily dosage of the composition or formulations of the present invention is generally prescribed by clinician; and it may vary according to patient's age, weight, sex and individual response to the drug, and severity of the disease etc. Generally, the dosage of administration for an adult is 0.05-5 mg of active ingredient per kg of body weight per day; preferably the dosage of administration is 0.1-0.5 mg of active ingredient per kg of body weight per day.

BEST MODE FOR CARRYING OUT THE INVENTION

The following examples are used for illustrating the present invention and not for limiting the invention.

Example 1

Preparation of Acetyl L-Carnitine Arsenate

Acetyl L-carnitine (35.3 g) was weighted and put in a flask (250 ml), into which 80 ml ethanol was added. The mixture was heated to dissolve completely. An ethanol solution containing 31.0 g arsenic acid was slowly and dropwise added into the solution of acetyl L-carnitine, continued to stir for a further 1 h after the addition, cooled to room temperature, and white crystals were precipitated. After grinding, 64.4 g of white powder was obtained. Yield: 97.1%. Melting temperature: 150.6° C.-152.1° C. $^1$H-NMR (DMSO, 500 MHz), δ 2.28 (m, 2H), 3.16 (m, 9H), 3.35 (m, 2H), 4.36 (m, 1H), 9.51 (s, 3H); IR: 3423 cm$^{-1}$, 2975 cm$^{-1}$, 2399 cm$^{-1}$, 1723 cm$^{-1}$, 1477 cm$^{-1}$, 1302 cm$^{-1}$, 1191 cm$^{-1}$, 1106 cm$^{-1}$, 879 cm$^{-1}$, 769 cm$^{-1}$.

Example 2

Preparation of DL-Carnitine Arsenate

DL-carnitine was used as a raw material instead of acetyl L-carnitine in example 1 according to the method of example 1 to get white powder of DL-carnitine arsenate. Yield: 89.7%. Melting temperature of the product: 136.1° C.-138.0° C. $^1$H-NMR (CD30D, 400 MHZ) δ: 2.67 (m, 2H), 3.27 (s, 9H), 3.49 (m, 2H), 4.67 (m, 1H); IR: 3490.3 m$^{-1}$, 3404.0 cm$^{-1}$, 3050 cm$^{-1}$, 2900 cm$^{-1}$, 1724 cm$^{-1}$, 1475 cm$^{-1}$, 1401 cm$^{-1}$, 1189 cm$^{-1}$, 1088 cm$^{-1}$, 975 cm$^{-1}$, 931 cm$^{-1}$.

Example 3

Preparation of L-Carnitine Arsenate

L-carnitine was used as a raw material instead of acetyl L-carnitine in example 1 according to the method of example 1 to get white crystals (without grinding). Yield: 97.0%. Melting temperature: 152.2° C.-153.1° C., [α]D$^{30}$=−14~−16 (10 g/100 ml, H$_2$O); 1H-NMR (CD30D, 400 MHZ), δ: 2.67 (m, 2H), 3.27 (s, 9H), 3.49 (m, 2H), 4.67 (m, 1H); IR: 3490.3 cm$^{-1}$, 3404.0 cm$^{-1}$, 3050 cm$^{-1}$, 2900 cm$^{-1}$, 1724 cm$^{-1}$, 1475 cm$^{-1}$, 1401 cm$^{-1}$, 1189 cm$^{-1}$, 1088 cm$^{-1}$, 975 cm$^{-1}$, 931 cm$^{-1}$.

When the angle of diffraction is 2θ in the X-ray diffraction patterns, the characteristic peaks are as follows:

10.238, d=8.6331, I/I0=36.9; 12.039, d=7.3451, I/I0=22.4; 12.500, d=7.0756, I/I0=53.7; 18.601, d=4.7662, I/I0=100.0; 19.519, d=4.5440, I/I0=35.1; 21.600, d=4.1108, I/I0=83.7; 22.021, d=4.0331, I/I0=23.6; 24.156, d=3.6806, I/I0=67.9; 25.220, d=3.5283, I/I0=27.3.

Solubility: 1 g of L-carnitine arsenate was completely dissolved in 5 ml of water and 65 ml of ethanol.

Example 4

Preparation of L-Carnitine Benzyl Ester Arsenate

L-carnitine benzyl ester was used as a raw material instead of acetyl L-carnitine in example 1 according to the method of example 1 to get a white solid powder of L-carnitine benzyl ester arsenate. Yield: 90.1%.

Example 5

An injection containing the active compound of the present invention was prepared based on the following method (all contents were measured by weight percentage): active compound 0.3%

| active compound | 0.3% |
|---|---|
| NaCl | 0.88% |
| Add water to | 100% |

The active compound and NaCl were added into water and stirred to dissolve, decolored with 0.2% active carbon to get the injection.

Example 6

Tablets or capsules containing the active compound of the present invention were prepared based on the following method (all contents were measured by weight percentage):

| active compound | 1.5% |
|---|---|
| lactose | 48% |
| microcrystalline cellulose | 45% |
| polyvinylpolypyrrolidone | 2% |
| hydroxypropyl methylcellulose | 2% |
| magnesium stearate | 1.5% |

Process: Hydroxypropyl methylcellulose was dissolved in ethanol to get a solution for granulation. The active compound was evenly mixed with the auxiliary materials except magnesium stearate, added into the said solution for granulation to form a soft material, sieved to get wet granules, dried at 60° C. with forced air, sieved for size stabilization, evenly mixed with magnesium stearate, and pressed into tablets with a tablet machine or filled into empty hard capsules.

Example 7

Patches containing the active compound of the present invention were prepared based on the following method (all contents were measured by weight percentage):

| active compound | 5% |
|---|---|
| polyacrylic ester | 95% |

The active compound was evenly dispersed in a polyacrylic ester glue solution, degassed, and the drug-containing glue was coated onto a backing membrane, dried, laminated with a protective film, and then cut for packaging.

Example 8

Ointments containing the active compound of the present invention were prepared based on the following method (all contents were measured by weight percentage):

| active compound | 5% |
|---|---|
| lanolin | 25% |
| vaseline | 35% |
| glycerol | 20% |
| 0.2% lauryl sodium sulfate solution | 15% |

The active compound was dissolved in a lauryl sodium sulfate solution, mixed with glycerol, and then evenly mixed with lanolin and vaseline.

Example 9

Poly(hydroxyethyl methacrylate) [P-(HEMA)]-Collagen protein sustained-release implants containing L-carnitine arsenate were prepared based on the following method

| L-carnitine arsenate | 1.4 g |
|---|---|
| collagen protein solution (20 g/L) | 15 ml |
| hydroxyethyl methylacrylate (HEMA) | 6 ml |
| solution of ammonium persulfate (60 g/L) | 1.0 ml |
| solution of sodium metabisulphite (12 g/L) | 1.0 ml |
| glycol | 10 ml |

L-carnitine arsenate was evenly mixed with all of the above liquids, and 1 ml of the liquid mixture was put into a 1.5 ml plastic centrifuge tube, placed in a constant temperature of 37° C. for 3 h. The obtained cream white, translucent, smooth, elastic gel was the poly(hydroxyethyl methacrylate) [P-(HEMA)]-Collagen protein implant containing L-carnitine arsenate.

Example 10

Liposomes containing L-carnitine arsenate were prepared based on the following method: Reverse phase evaporation was used for preparation. Lecithin and cholesterol were dissolved in 10 ml ether and L-carnitine arsenate was dissolved in 4 ml saline. These two solutions were mixed in a flask, and oscillated under ultrasound for 2 min. Ether was removed at 40° C. by vacuum rotary evaporation to get a viscous solution, then 6 ml saline was added, oscillated under ultrasound for 2 min, and continued to rotationally evaporate under ordinary pressure to obtain the liposome suspension emulsion containing L-carnitine arsenate.

Example 11

Pharmacodynamics Test of Arsenic Compounds (1) Cell Proliferation Test

Logarithmic phase HL-60 cells ($1 \times 10^5$/ml) were inoculated in a 96 well round bottom culture plate, with 100 ul per well. Tested drugs with different concentrations were added, and repeated four wells for each drug concentration group, then continued to culture in a $CO_2$ incubator. Cell proliferation was detected by MTT method 48 h after culture. 15 ul MTT (5 mg/ml) was added in each well, and continued to culture for 4 h. Suspension in the well was collected, centrifuged, and supernatant was discarded. 100 ul of DMSO was added into each well to completely dissolve formazan particles. The solution was sucked into the original well, the absorbance at 492 nm was detected by ELISA, and the inhibiting rate was calculated according to the formula CI=(1-A test group /A control group)×100%.

The results were showing as below:

TABLE 1 the effect of L-carnitine arsenate on HL-60 cell proliferation

| Groups | A492 | Inhibiting rate |
|---|---|---|
| Control | 0.34 ± 0.005 | — |
| 7.5 uM | 0.322 ± 0.009 | 5.2 |
| 15 uM | 0.285 ± 0.011* | 16.3 |
| 30 uM | 0.239 ± 0.007* | 29.7 |
| 60 uM | 0.175 ± 0.008* | 48.4 |
| 120 uM | 0.128 ± 0.012* | 62.5 |

TABLE 2 the effect of $Na_3AsO_4$ on HL-60 cell proliferation

| Groups | A492 | Inhibiting rate |
|---|---|---|
| Control | 0.34 ± 0.005 | — |
| 7.5 uM | 0.331 ± 0.003 | 2.5 |
| 15 uM | 0.313 ± 0.011** | 7.9 |
| 30 uM | 0.293 ± 0.015** | 13.9 |
| 60 uM | 0.257 ± 0.011* | 24.5 |
| 120 uM | 0.215 ± 0.006* | 36.8 |

Wherein
*P < 0.01,
**P < 0.05.

It could be seen from the results shown in table 1 and table 2 that both drugs have certain inhibiting effects on cell proliferation. However, L-carnitine arsenate is apparently more effective than $Na_3AsO_4$ under the same concentration; a concentration-dependent manner was shown. While $Na_3AsO_4$ had weak and slight efficiency, with only about 37% inhibiting rate even at such a high concentration of 120 uM.

(2) Cell Viability Test

Logarithmic phase HL-60 cells ($1 \times 10^5$/ml) were inoculated in a 24 well cell culture plate, with 0.5 ml per well. Drugs with different concentrations were added. 0.2 ml of cell suspension in each group was taken respectively at the fourth day after adding the drugs, and 0.5 ml of 0.4% Trypan blue solution and 0.3 ml of PBS were added and mixed well. Then the mixture was left in the room temperature for 10 min, live cell numbers and total cell numbers were counted with blood counting chamber, and live cell rate were calculated. Live cell rate=live cell number/total cell number×100%

TABLE 3 live cell rate at 4 d after administration (%)

| Drugs | Control | 7.5 uM | 15 uM | 30 uM | 60 uM | 120 uM |
|---|---|---|---|---|---|---|
| L-carnitine arsenate | 96.08 | 95.45 | 90.32 | 80.42 | 69.97 | 50.29 |
| $Na_3AsO_4$ | 96.08 | 93.11 | 89.06 | 75.36 | 60.06 | 43.11 |

The results were shown in table 3:

It could be seen from the results shown in table 3 that the live cell rates of the L-carniniate arseniate groups were significantly higher than that of the $Na_3AsO_4$ groups at the same concentrations, especially higher concentrations at which the pharmacodynamic effects occurs. Combined with the proliferation test, we found that the L-canitine arsenate group has obvious proliferation inhibiting effect and weak cell toxicity. However, the proliferation inhibiting effect of $Na_3AsO_4$ group was probably caused by its toxic effect.

The invention claimed is:

1. An arsenic compound having a structure of formula (I) or a levoisomer, a dextroisomer or a racemate thereof:

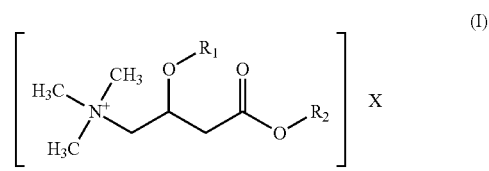

(I)

wherein $R_1$ is independently H, a linear or branched $C_2$-$C_{20}$ alkylacyl group, or a $C_7$-$C_{12}$ phenylalkylacyl group;

$R_2$ is independently H, a linear or branched $C_2$-$C_8$ alkyl group, or a $C_7$-$C_{12}$ phenylalkyl group; and X is selected from the group consisting of $H_2AsO_4^-$, $HLiAsO_4^-$, $HKAsO_4^-$, $HNaAsO_4^-$, $Li_2AsO_4^-$, $K_2AsO_4^-$, $Na_2AsO_4^-$, $CaAsO_4^-$, $MgAsO_4^-$, $AsO_2^-$, $(NH_4)_2AsO_4^-$, and $(NH_4)HAsO_4^-$.

2. The arsenic compound of claim 1, wherein the arsenic compound is of formula (II) or a laevoisomer, a dextroisomer or a racemate thereof:

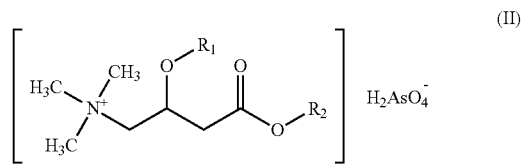

(II)

wherein $R_1$ is independently H, a linear or branched $C_2$-$C_{20}$ alkylacyl group, or a $C_7$-$C_{12}$ phenylalkylacyl group;

$R_2$ is independently H, a linear or branched $C_2$-$C_8$ alkyl group, or a $C_7$-$C_{12}$ phenylalkyl group.

3. The arsenic compound of claim 2, wherein $R_1$ is acetyl, propionyl, butyryl, valeryl, isovaleryl, lauroyl, tetradecanoyl, palmitoyl, stearyl, benzoyl, phenylacetyl, phenyl propionyl, phenyl butyryl, phenyl valeryl or phenyl isovaleryl; and $R_2$ is ethyl, propyl, butyl, pentyl, isopentyl, benzyl, phenethyl, phenylpropyl, phenylbutyl, phenylpentyl or phenylisopentyl; and wherein the compound is selected from laevoisomers, dextroisomers and racemates.

4. The arsenic compound of claim 1, wherein the arsenic compound is a white crystal or an amorphous powder.

5. The arsenic compound of claim 4, wherein the crystal of the compound is acetyl L-carnitine arsenate, DL-carnitine arsenate, or L-carnitine arsenate.

6. The arsenic compound of claim 5, wherein the crystal of the compound has the following characteristic peaks of x-ray diffraction pattern: 10.238, d=8.6331, I/I0=36.9; 12.039, d=7.3451, I/I0=22.4; 12.500, d=7.0756, I/I0=53.7; 18.601, d=4.7662, I/I0=100.0; 19.519, d=4.5440, I/I0=35.1; 21.600, d=4.1108, I/I0=83.7; 22.021, d=4.0331, I/I0=23.6; 24.156, d=3.6808, I/I0=67.9; 25.220, d=3.5283, I/I0=27.3.

7. A pharmaceutical composition, which contains an arsenic compound of claim 1 as an active ingredient and a pharmaceutical carrier.

8. A pharmaceutical formulation prepared by a pharmaceutical composition of claim 7, wherein dosage forms of the pharmaceutical formulation include oral preparations, injections or topical preparations, and wherein:
   (1) the oral preparations include ordinary tablets, sustained release tablets, granules, hard or soft capsules, syrups, solutions, and emulsions; wherein carriers of the oral preparations include fillers, disintegrating agents, adhesives, lubricants, coloring agents, flavoring agents or other conventional additives, which specifically include starch, lactose, microcrystalline cellulose, sodium carboxymethyl starch, crosslinked polyvinylpyrrolidone, polyvinylpyrrolidone, hydroxypropyl methylcellulose, magnesium stearate, silica and polysorbate 80, and sodium lauryl sulfate;
   (2) the injections include sterile aqueous solutions for injection, sterile oil-in-water microemulsions for injection and sterile powders for injection; wherein carriers of the injections include solvents for injection and additives for injection, and the solvents for injection which specially include water for injection, oils for injection such as soybean oil, solubilizers for injection such as ethanol, propylene glycol, polyethylene glycol, glycerin, and isotonic substances such as sodium chloride, glucose; and
   (3) the topical preparations are patches, suppositories, creams, ointments, gels, solutions, suspensions or targeting preparations, wherein the said targeting preparations include liposomes, microspheres, nanoparticles, inclusions and conjugates of monoclonal antibodies; wherein carriers of topical preparations include conventional pharmaceutical carriers used for topical administration.

9. A method for administering a pharmaceutical formulation of claim 8, which comprises one or more of intravenous administration, intramuscular administration, intraperitoneal administration, subcutaneous administration, oral administration, rectal suppository insertion method, intravaginal suppository insertion method, targeted drug delivery, inhalation, gavage, nasal feeding, sublingual administration, dripping method, micro-needle administration, continuous drug delivery system, and topical administration, a form for topical administration includes transdermal preparations or implantable continuous drug release system, wherein, the carrier for transdermal preparations includes framework materials such as hydrophobic polysiloxane, hydrophilic polyvinyl alcohol; controlled release membrane materials such as polysiloxane, ethylene-vinyl acetate copolymer, pressure-sensitive adhesives such as polyisobutylene, polysiloxane and polyacrylate, active ingredients being generally dispersed in the pressure-sensitive adhesives; polymer materials for the implantable continuous drug release system include polylactic acid glycolic acid copolymer, polyethylene glycol polylactic acid copolymers, polylactic acid/polycaprolactone, poly[(tetramethylene-co-ϵ-caprolactone) carbonate], poly-butyrolactone valerolactone, polydioxanone (PDS), poly-3-hydroxybutyrate (PHB), poly-L-lactic acid(PLLA), polyglycolic acid (PGA), poly-ϵ-caprolactone(PCL), polycaprolactone/poly (glycolide-co-lactide) (PCL/PLGA), and hydroxyethyl methacrylate (HEMA).

10. A method of treating leukemia comprising administering the compound of claim 1.

11. The method of claim 9, wherein the dosage of administration for an adult is 0.001-50 mg of active ingredient per kg of body weight per day.

12. The method of claim 11, wherein the dosage of administration for an adult is 0.05-5 mg of active ingredient per kg of body weight per day.

13. The method of claim 12, wherein the dosage of administration for an adult is 0.1-0.5 mg of active ingredient per kg of body weight per day.

14. A method for preparing an arsenic compound or a crystal thereof of claim 2, which includes the steps of:
   a) dissolving a compound of formula (III) in an organic solvent to form a solution;

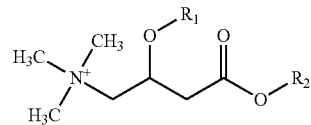

b) dropwise adding arsenic acid or optionally a compound X of claim 1 into the solution obtained in step a) under stirring;
   c) separating out a salt of formula (II);
   d) crystallizing the salt of step c) in an organic solvent to obtain a crystal of the arsenic compound.

15. The method of claim 14, wherein the organic solvent is a $C_{1-5}$ alcohol.

16. The method of claim 15, wherein the alcohol is ethanol.

17. The arsenic compound of claim 2, wherein the arsenic compound is a white crystal or an amorphous powder.

18. A pharmaceutical composition comprising the arsenic compound of claim 6 and a pharmaceutical carrier.

19. A method of treating leukemia comprising administering the compound of claim 6 to a patient in need of treatment of leukemia.

20. A method of treating leukemia comprising administering a composition of claim 7 to a patient in need of treatment of leukemia.

21. The method of claim 10, wherein the dosage of administration for an adult is 0.001-50 mg of active ingredient per kg of body weight per day.

* * * * *